United States Patent
Komma

(10) Patent No.: US 6,176,887 B1
(45) Date of Patent: Jan. 23, 2001

(54) SILICATE DENTAL CERAMIC-BASED BLASTING MEDIUM

(75) Inventor: Ottmar Komma, Niddatal (DE)

(73) Assignees: Degussa Hüls Aktiengesellschaft, Frankfurt am Main; Ducera Dental-GmbH & Co. KG, Rosbach v.d.H, both of (DE)

(*) Notice: Under 35 U.S.C. 154(b), the term of this patent shall be extended for 0 days.

(21) Appl. No.: 09/363,393

(22) Filed: Jul. 29, 1999

(30) Foreign Application Priority Data

Jul. 29, 1998 (DE) ................................. 198 34 106

(51) Int. Cl.⁷ .................. C09K 3/14; A61K 6/00; A61K 7/16
(52) U.S. Cl. .................. 51/308; 106/3; 106/35; 424/49
(58) Field of Search .................. 51/308; 106/3, 106/35; 451/36, 38; 424/49

(56) References Cited

U.S. PATENT DOCUMENTS

| | | | |
|---|---|---|---|
| 2,489,848 | * 11/1949 | Bacon et al. | 51/308 |
| 3,892,843 | * 7/1975 | Muhler et al. | 424/52 |
| 4,044,507 | * 8/1977 | Cox et al. | 51/308 |
| 4,579,530 | 4/1986 | McLaughlin | 433/223 |
| 5,024,711 | * 6/1991 | Gasser et al. | 51/308 |
| 5,380,356 | 1/1995 | Gundlach et al. | 106/3 |
| 5,405,555 | * 4/1995 | Riker | 252/607 |
| 5,512,071 | * 4/1996 | Yam et al. | 51/308 |
| 5,827,114 | * 10/1998 | Yam et al. | 451/75 |

FOREIGN PATENT DOCUMENTS

| | | |
|---|---|---|
| 3802042 | 7/1989 | (DE) . |
| 19603196 | 8/1997 | (DE) . |

* cited by examiner

*Primary Examiner*—Michael Marcheschi
(74) *Attorney, Agent, or Firm*—Smith Gambrell & Russell, LLP

(57) ABSTRACT

A silicate dental ceramic-based blasting medium for the improvement of the adhesive bond between fire-on ceramic and alloy. In contrast to the traditionally used $Al_2O_3$ blasting medium, the complete sealing of the alloy-ceramic contact layer is guaranteed. In this way, the penetration of moisture (from the milieu of the mouth) in the contact layer is prevented. The phenomenon of bubble formation known from practice in dental work worn on a trial basis can thus be stopped after correction firing.

10 Claims, No Drawings

SILICATE DENTAL CERAMIC-BASED BLASTING MEDIUM

INTRODUCTION AND BACKGROUND

The present invention concerns a silicate dental ceramic-based blasting medium for the improvement of the adhesive bond between a fired-on ceramic and alloy.

According to the state of the art, individual metal substructures for prosthetic teeth are manufactured according to the investment casting [lost wax] process. In this process, the eventual metal substructure is first modeled in a 1:1 wax scale model, is provided with sprue channels and is embedded in a commercially available fireproof embedding compound in a ring muffle.

After the setup reaction of the embedding compound, the ring muffle is heated in a suitable burn-out oven in order to completely expel the wax and create a hollow mold. A molten dental alloy is introduced into this mold using a centrifugal caster.

After cool-down and removal of the embedding compound from the metal dental substructure, it is finished with rotary tools and checked for conformity to the master model. As a rule, blasting with a blasting medium comes next, followed by an oxidation process and an additional blasting step. Predominantly aluminum oxide ($Al_2O_3$) with a particle size of about 110 $\mu$m is used as the blasting medium. The purpose of this surface treatment is the improvement of the adhesive bond between the first fired-on ceramic layer (opaque) and the alloy by retention (roughened surface) as well as by formation of adhesive oxides (oxide firing). By application of the dentin core as well as the compound for the cutting edge, each followed by oven firings, the natural tooth is replicated in the end to be as natural looking as possible.

In order to guarantee a good bond between alloy and ceramic, a so-called adhesive firing is also recommended by dental ceramic manufacturers. As in the normal process, a thin opaque layer is first applied to the alloy and then fired at higher temperatures, specifically about 30–50° C. above the normal firing temperature. In this way, the opaque is converted into a low viscosity state, whereby all cavities and uneven places are wetted. After cool-down, a glassy, smooth ceramic coating forms on the metal substructure. Depending on the manufacturer, the adhesive firing can also be executed with a compound offered for this which is characterized as "adhesive bond"—a special bonding agent.

An overfiring of the opaque is unproblematic as far as heat resistance, substructure deformation and fitting are concerned, since, in spite of increased firing temperatures (e.g. 980° C.), the interval to the solidus point of the alloy amounts to more than 200° C. However, it appears differently in the so-called bio-alloys which have been present on the market for several years. This alloy type has a gold portion of over 75% by weight and is correspondingly gold colored. As a result, alloy technology requires the solidus point to be lowered 250 to 350° C. in relation to the classic dental alloys to an absolute value between 900 and 1000° C. The bio-alloys are faced with specially developed, low-melting-point ceramics in order to guarantee the substructure stability and compatibility of the thermal expansion coefficient.

An adhesive firing analogous to the technique of overfiring typical for the classic dental alloys increases the probability of deformation in the dental substructure and for this reason is executed at a correspondingly low temperature for the bio-alloys.

However, in combination with the practice, which was introduced for these new alloy types, of "wearing the prosthetic tooth on a trial basis", an increased bubble formation, compared to the classic metal-ceramic system, is observed in the finish firing. In this process, the prosthetic tooth is temporarily installed in the patient's mouth for a certain period of time (from a few days to a few months) by the dentist for the purpose of reviewing the bio-compatibility and occlusion. After this trial time, the dental work (crowns or bridges) goes back to the dental technology laboratory and is corrected according to dental technology processes and lastly is subjected to a finish or glaze firing.

In the blasting of the metal substructure, residues of the blasting medium remain on or in the surface of the alloy and can be detected by scanning electron microscopic examination and x-ray fluorescence analysis. It is assumed that the additional steps of surface conditioning for the formation of residual pore channels between alloy and first ceramic layer (opaque or adhesive bond) are required with the use of $Al_2O_3$ blasting medium, but also with other inert hard materials such as silicon carbide (SiC) or boron carbide ($B_4C$) fundamentally suited for this. Moisture is sucked into the channels by capillary forces and the bubbles observed many times in practice after wearing the prosthesis on a trial basis are generated in the subsequent correction firing.

Surprisingly, it was discovered that, after the replacement of the customarily used blasting medium with a silicate dental ceramic-based blasting medium, the bubble formation after wearing of the prosthetic teeth on a trial basis and after subsequent correction firing can be completely suppressed. The disadvantage of the metal-ceramic bio-alloys, compared to the traditional high-melting-point alloy—facing ceramic systems, is thus eliminated.

SUMMARY OF THE INVENTION

A feature of the invention is a glass ceramic silicate blasting medium which improves the wetting properties between alloy and ceramic (opaque) in comparison to the conventionally used $Al_2O_3$ blasting medium. In contrast to the latter, the contact surface between the two components is completely "sealed".

Another feature of the invention is a blasting medium for use in dental technology, which is characterized by the fact that it consists of fine particle silicate dental ceramic.

Still a further feature of the invention is the use of such a blasting medium for surface conditioning of metal substructures to be faced with dental ceramic, in particular in low-melting-point alloy—fire-on-ceramic systems.

Any silicate dental ceramic is suitable as a blasting medium in the sense of the invention as long as it is available in the essentially homogenous composition of the ceramic components in a particular form typical for blasting media. This assumes that the dental ceramic is present in fine-particle form after sintering or from the melt, or can be milled to the corresponding particle size, which as a rule is the case.

The blasting medium according to the invention has a suitable particle size of 50 to 200 $\mu$m, preferably 100 to 150 $\mu$m.

The blasting medium particles are irregular in their outer form and are mostly in the form of splinters.

Preferably, the blasting medium consists of

| | |
|---|---|
| 40–98% by weight | $SiO_2$ |
| 2–25% by weight | $Me(III)_2O_3$ |
| 0–30% by weight | $Me(I)_2O$ |
| 0–20% by weight | $Me(II)O$ |
| 0–30% by weight | $Me(IV)O_2$ |
| 0–8% by weight | $B_2O_3$ |
| 0–15% by weight | $P_2O_5$ |
| 0–3% by weight | F | in which $Me(III)_2O_3$ stands for $Al_2O_3$, $La_2O_3$ and $Sb_2O_3$;
$Me(I)_2O$ stands for $K_2O$, $Na_2O$ and $Li_2O$;
$Me(II)O$ stands for CaO, BaO, MgO, ZnO and SrO; and
$Me(IV)O_2$ stands for $TiO_2$, $ZrO_2$, $CeO_2$ and $SnO_2$.

In an especially preferred version, the blasting medium has the following composition:

| | |
|---|---|
| 56–63% by weight | $SiO_2$ |
| 8–24% by weight | $Al_2O_3$ |
| 7–14% by weight | $K_2O$ |
| 4–14% by weight | $Na_2O$ |
| 0–2% by weight | $Li_2O$ |
| 0–8% by weight | $B_2O_3$ |
| 0–1.5% by weight | CaO |
| 0–1.5% by weight | $TiO_2$ |
| 0–0.5% by weight | $CeO_2$ |
| 0–0.6% by weight | $Sb_2O_3$ |
| 0–3% by weight | F |

DETAILED DESCRIPTION OF INVENTION

It is assumed that, in the blasting of dental metal substructures with the blasting media according to the invention, residual blasting media remaining on or in the metal surface leads to an intensive bond of the fire-on ceramic to the metal substructure. This is shown in, among other things, a clear increase of the adhesion values compared to substructures blasted with $Al_2O_3$. In particular, no residual pore channels form in this process, in contrast to $Al_2O_3$ blasting media, in which moisture is later drawn in, which in a subsequent finish firing can lead to bubble formation. The dental ceramic blasting medium according to the invention instead guarantees that the contact layer between metal substructure and ceramic (opaque) is free of pores and completely "sealed".

The blasting medium according to the invention can accordingly be used very advantageously in the surface conditioning of metal substructures to be faced with dental ceramic. This advantage is especially noticeable with low-melting-point alloy—fire-on-ceramic systems.

By completely sealing opaque-alloy contact layer, the penetration of moisture into it is prevented; the bubble formation after wearing the prosthetic teeth on a trial basis and subsequent correction, or finish firing is stopped.

The blasting process with the blasting medium according to the invention occurs under standard conditions with standard equipment.

EXAMPLE 1

Table 1 below shows the compositions of blasting media according to the invention based on fine-particle (100–150 $\mu$m) silicate dental ceramic.

They are obtained by quenching melts of correspondingly composed ceramic compounds in water, then milling, e.g. in a ball mill, and by classification of the desired particle size range.

TABLE 1

| Blasting medium particle size 100–150 $\mu$m | No. 1 | No. 2 | No. 3 |
|---|---|---|---|
| $SiO_2$ | 58.1 | 62.4 | 57.8 |
| $Al_2O_3$ | 14.1 | 8.8 | 22.2 |
| $K_2O$ | 13.0 | 11.6 | 8.9 |
| $Na_2O$ | 5.7 | 10.6 | 11.0 |
| $Li_2O$ | 0.9 | 1.0 | — |
| $B_2O_3$ | 6.9 | 1.0 | — |
| CaO | 0.4 | 1.0 | 0.1 |
| $TiO_2$ | 0.1 | 1.1 | — |
| $CeO_2$ | 0.3 | 0.2 | — |
| $Sb_2O_3$ | 0.4 | 0.3 | — |
| F | — | 2 | — |

EXAMPLE 2

In order to simulate in the laboratory the bubble formation after wearing the prosthetic teeth on a trial basis, the following experiment was executed:

Production and facing of crowns occurred according to typical operating instructions or manufacturer specifications from a commercially available low-melting-point, high-gold-content dental alloy (DEGUNORM®, Degussa) and a commercially available paste opaque based on low-melting-point dental ceramic (DUCERAGOLD®, Ducera). 10 crowns each were blasted with the blasting media according to the invention as per Example 1 and comparable to $Al_2O_3$ (110 $\mu$m) as well as to SiC (110 $\mu$m) and $B_4C$ (110 $\mu$m). The work was done with a commercial blasting device of the Bego company (Ministar; pressure: 2 bar; 1.2 mm blasting nozzle).

The crowns were then stored under pressure (6 bar) at 80° C. in artificial saliva for 20 hours. After this treatment, the crowns were dried briefly and then fired again (correction firing). The results are summarized in Table 2 according to the particular blasting medium.

TABLE 2

| Blasting medium | Number of defective crowns |
|---|---|
| Blasting medium no. 1 | 0 |
| Blasting medium no. 2 | 0 |
| Blasting medium no. 3 | 0 |
| $Al_2O_3$ | 10 |
| SiC | 10 |
| $B_4C$ | 10 |

Further variations and modifications of the foregoing will be apparent to those skilled in the art and are intended to be encompassed by the claims appended hereto.

German priority application 198 34 106.7 filed Jul. 29, 1998 is relied on and incorporated herein by reference.

I claim:

1. A fine-particle silicate dental ceramic blasting medium for use in dental technology, consisting essentially of the essential components:
   40–98% by weight $SiO_2$;
   2–25% by weight $Me(III)_2O_3$, being at least one member selected from the group consisting of $Al_2O_3$, $La_2O_3$ and $Sb_2O_3$;

and $B_2O_3$, wherein said $B_2O_3$ is present in an amount of no more than 8% by weight; and wherein the blasting medium can optionally contain the following components:

0–30% by weight $Me(I)_2O$, being at least one member selected from the group consisting of $K_2O$, $Na_2O$ and $Li_2O$;

0–20% by weight $Me(II)O$, being at least one member selected from the group consisting of CaO, BaO, MgO, ZnO and SrO;

0–30% by weight $Me(IV)O_2$, being at least one member selected from the group consisting of $TiO_2$, $ZrO_2$, $CeO_2$ and $SnO_2$;

0–15% by weight $P_2O_5$; and

0–3% by weight F.

2. The blasting medium according to claim 1, which has a particle size from 50 to 200 µm.

3. The blasting medium according to claim 1, which has a particle size from 100 to 150 µm.

4. The blasting medium according to claim 1, consisting essentially of:

56–63% by weight $SiO_2$;
8–24% by weight $Al_2O_3$;
7–14% by weight $K_2O$;
4–14% by weight $Na_2O$;
0–2% by weight $Li_2O$;
1–8% by weight $B_2O_3$;
0–1.5% by weight CaO;
0–1.5% by weight $TiO_2$;
0–0.5% by weight $CeO_2$;
0–0.6% by weight $Sb_2O_3$; and
0–3% by weight F.

5. The blasting medium according to claim 2, consisting essentially of:

56–63% by weight $SiO_2$;
8–24% by weight $Al_2O_3$;
7–14% by weight $K_2O$;
4–14% by weight $Na_2O$;
0–2% by weight $Li_2O$;
1–8% by weight $B_2O_3$;
0–1.5% by weight CaO;
0–1.5% by weight $TiO_2$;
0–0.5% by weight $CeO_2$;
0–0.6% by weight $Sb_2O_3$; and
0–3% by weight F.

6. The blasting medium according to claim 3, consisting essentially of:

56–63% by weight $SiO_2$;
8–24% by weight $Al_2O_3$;
7–14% by weight $K_2O$;
4–14% by weight $Na_2O$;
0–2% by weight $Li_2O$;
1–8% by weight $B_2O_3$;
0–1.5% by weight CaO;
0–1.5% by weight $TiO_2$;
0–0.5% by weight $CeO_2$;
0–0.6% by weight $Sb_2O_3$; and
0–3% by weight F.

7. A process for surface conditioning of metal substructures to be faced with dental ceramic, comprising blasting a surface to be faced with a dental ceramic with the blasting medium of claim 1.

8. The process according to claim 7 further comprising drying said surface and firing said surface at a sufficient temperature to obtain a conditioned product.

9. A dental crown produced by the process of claim 7.

10. A dental crown produced by the process of claim 8.

* * * * *